US005957839A

United States Patent [19]
Kruse et al.

[11] Patent Number: 5,957,839
[45] Date of Patent: Sep. 28, 1999

[54] APPARATUS AND METHOD FOR CONTINUOUS MONITORING OF TISSUE GAS COMPOSITION AND PH USING RECIRCULATING GAS TONOMETRY

[75] Inventors: James Alexander Kruse, Bloomfield Hills; Jorge Alberto Guzman, Farmington Hills, both of Mich.

[73] Assignee: Wayne State University, Detroit, Mich.

[21] Appl. No.: 09/026,360

[22] Filed: Feb. 19, 1998

Related U.S. Application Data

[63] Continuation-in-part of application No. 08/390,406, Feb. 16, 1995, Pat. No. 5,743,259.

[51] Int. Cl.[6] ........................................................ A61B 5/00
[52] U.S. Cl. .......................... 600/309; 600/350; 600/353; 600/361; 600/366
[58] Field of Search ...................................... 600/309–312, 600/316, 322–23, 325–28, 345–48, 353, 360–64, 473, 476, 350, 365, 366

[56] References Cited

U.S. PATENT DOCUMENTS

| 4,643,192 | 2/1987 | Fiddian-Green . |
| 4,928,694 | 5/1990 | Maxwell . |
| 5,058,416 | 10/1991 | Engelhardt et al. . |
| 5,423,320 | 6/1995 | Salzman et al. . |
| 5,479,923 | 1/1996 | Rantala . |

OTHER PUBLICATIONS

A461, vol. 83, Anesthesiology No. 3A 09/195. "A New Method for Continuous Intramucosal PCO₂ –Measurement in the Gastrointestinal Tract".

A.M. Dawson, et al., "Small Bowel Tonometry: Assessment of Small Gut Mucosal Oxygen Tension in Dog and Man", 206 Nature 943–44 (1965).

A.B. Johan Groeneveld and Jeroen J. Kolkman, "Splanchnic Tonometry: A Review of Physiology, Methodology, and Clinical Applications", Journal of Critical Care, vol. 9.

Cinda H. Clark and Guillermo Gutierrez, "Gastric Intramucosla pH: A Noninvasive Method for the Indirect Measurement of Tissue Oxygenation", Amer. Jrnl. of Crit.

David R. Dantzker, "The Gastrointestinal Tract the Canary of the Body?", JAMA, Sep. 8, 1993—vol. 270, 1247–1248.

Michael C. Chang et al., "Gastric Tonometry Supplements Information Provided by Systemic Indicators of Oxygen Transport", The Journal of Trauma, 488–494, 1994.

Paul E. Marik, "Gastsric Intermucosal pH* A Better Predictor of Multiorgan Dysfunction Syn. and Death than Oxygen–Derived Cari. in Pat. with Sepsis", Univ. of W.

Nicholas Maynard, et al. "Assessment of Splanchnic Oxygenation by Gastric Tonometry in Patients with Acute Circulatory Failure", JAMA, vol. 270, No. 10, Sep. 8, 1993.

Guillermo R. Doglio, et al., "Gastric Mucosal pH as a Prognostic Index of Mortality in Critically Ill Patients", Critical Care Medicine, vol. 19, No. 8 1037–1040 (1991).

Comprehensive Instructions for Use, Trip NGS Catheter, Catalog No. 2002–48–16, Tonometrics, Inc.

James A. Kruse, et al. "Relationship Between the Apparent Dissociation Constant of Blood Carbonic Acid and Severity of Illness", The Journal of Lab. & Clin. Medicine, (1989).

*Primary Examiner*—John P. Lacyk
*Attorney, Agent, or Firm*—Brooks & Kushman P.C.

[57] ABSTRACT

A tonometry catheter apparatus comprises an elongate, flexible, multilumen tube having a proximal end to be positioned outside the human body and a distal end to be positioned within a portion of the human body. Provided at the distal end are an ingress lumen through which gas may enter the tube, and an egress lumen through which gas may exit the tube. A hollow connecting member links the ingress lumen and the egress lumen to define a sampling circuit through which the gas may continuously recirculate. In one embodiment, the distal end of the tube is provided with a distensible, gas-permeable vessel in communication with the ingress and egress lumens. In an alternative embodiment, an extracorporeal gas-permeable membrane links the sampling circuit to a separate, gas-containing analyzing circuit. In each embodiment, a pump is provided for propelling gas through the circuits, and a sensor continuously quantifies the level of gas within the circuits.

41 Claims, 5 Drawing Sheets

APPARATUS AND METHOD FOR CONTINUOUS MONITORING OF TISSUE GAS COMPOSITION AND PH USING RECIRCULATING GAS TONOMETRY

CROSS-REFERENCE TO RELATED APPLICATION

This application is a continuation-in-part of U.S. patent application Ser. No. 08/390,406, filed Feb. 16, 1995, now U.S. Pat. No. 5,743,259 entitled "Apparatus and Method For Continuous Monitoring of Tissue Carbon Dioxide and pH Using Capnometric Recirculating Gas Tonometry", which is assigned to the assignee of the present invention and which is hereby incorporated by reference.

TECHNICAL FIELD

This invention relates to a method and apparatus for continuous monitoring of tissue gas composition and pH using intracorporeal or extracorporeal recirculating gas tonometry.

BACKGROUND ART

Most cells, tissues, and organs of the human body require oxygen to carry out their normal physiologic functions and to maintain viability. This oxygen is obtained from the atmosphere by the lungs, carried predominantly by hemoglobin molecules in the blood, and delivered to the cells, tissues, and organs of the body by the circulatory system. If the lungs can not provide sufficient oxygen to the blood, if there is insufficient hemoglobin in the blood (i.e., anemia) to carry sufficient oxygen, if the heart cannot pump an adequate volume of blood over time to the various organs of the body, or if there is blockage of blood flow to one or more regions of the circulation, the affected cells will suffer from lack of adequate oxygen, a condition known as tissue hypoxia.

An important goal in the clinical management of critically ill patients is ensuring the adequacy of tissue oxygenation. A variety of means are in use to help achieve this goal. Among these, pulmonary artery catheterization is commonly used to allow determination of cardiac output, mixed venous oxygen saturation and partial pressure, and derivation of oxygenation transport variables such as systemic oxygen delivery, systemic oxygen consumption, and systemic oxygen extraction. However, these conventional hemodynamic and oxygen-derived parameters can be insensitive to mild, moderate, early, or compensated stages of perfusion failure, and to regional tissue hypoperfusion, including ischemia, or hypoxia involving areas such as the gastro-intestinal tract.

If tissue hypoxia is sufficiently severe, the hypoxic cells produce lactic acid. This allows the cells to produce needed energy in the absence of oxygen, and provides a temporary means of maintaining cellular function and viability. It is temporary because this excessive acid production results in a decrease of the pH within and around the cells, and this decrease in pH will itself eventually threaten the functional capacity and viability of the affected cells. Thus, detecting a decrease in the pH inside cells comprising a tissue or organ can serve as an indicator of tissue hypoxia.

Measurement of the pH of the cells lining the stomach (gastric intramucosal pH), intestines, or other organs or tissues of the body can be performed using a technique known as hollow viscus tonometry, in which a walled chamber is placed within a hollow organ such as the stomach. The walled chamber, which may be in the form of a balloon, is constructed of material that is permeable to carbon dioxide ($CO_2$) gas, but effectively impermeable to liquid. When filled with a liquid such as water or saline solution and situated within the hollow viscus, such a balloon will allow the passage of $CO_2$ gas from the hollow viscus to pass through the membrane of the balloon and become dissolved in the liquid solution contained within the balloon. In time, the level of $CO_2$ in solution within the balloon will equal or be proportional to the level of $CO_2$ within the hollow viscus. Because biological membranes, including the membranes that compose the surface of the cells lining the stomach and other hollow organs, are also permeable to $CO_2$ gas, the level of $CO_2$ within the hollow viscus will, under certain undisturbed circumstances, be equal to or approximately equal to the level of $CO_2$ within the cells comprising or lining the viscus.

Thus, if the liquid-filled balloon is allowed to sit within a hollow viscus such as the stomach or intestine for a sufficient period of time, and then the liquid is aspirated from the balloon by a catheter connected to the balloon and analyzed in a laboratory to determine the level of $CO_2$ gas dissolved within the liquid, the level of $CO_2$ gas inside the cells lining the viscus (intramucosal $pCO_2$) can be ascertained. If intramucosal $pCO_2$ is known, then intramucosal pH can be determined using a mathematical formula that relates pH to $pCO_2$. This formula also requires that a third variable is known, namely the concentration of bicarbonate ions inside the cells comprising or lining the viscus. This intracellular bicarbonate concentration is equal to or approximately equal to the concentration of bicarbonate ions in arterial blood, serum, or plasma, and the latter can be readily determined by a blood test.

As is common clinical practice, this blood test is frequently performed in most hospitalized, critically ill patients treated in an intensive care unit setting, often being performed daily or even several times each day. The bicarbonate concentration can be obtained by direct measurement, or calculated from the results of other blood tests using a mathematical equation (see Kruse J. A., Hukku P., Carlson R. W.: "Relationship Between The Apparent Dissociation Constant Of Blood Carbonic Acid And Severity Of Illness," 114 *J. Lab. Clin. Med.* 568–574 (1989)).

According to information from scientific studies that have been reported in the published biomedical literature, tonometry is a useful means of evaluating splanchnic intramucosal $pCO_2$ and pH, referring to the cells lining or comprising certain portions of the gastrointestinal tract and certain adjacent organs or tissues, thereby indirectly evaluating the adequacy of splanchnic blood flow and oxygenation. In trauma, shock, and sepsis, the body selectively diverts splanchnic blood flow to the heart, lungs, and brain, thus making the gastrointestinal tract a sensitive and early diagnostic indicator of systemic ischemia, hypoperfusion, and hypoxia. Furthermore, the available information indicates that determination of tissue pH is a valuable prognostic indicator of survival among critically ill patients hospitalized in the intensive care unit setting, and that it is a better prognostic indicator than any of the conventional hemodynamic and oxygen-derived physiological variables.

U.S. Pat. No. 4,643,192 is illustrative of tonometric methods, and is incorporated herein by reference. An illustrative device is described in Catalog No. 2002-48-16, TRIP® NGS CATHETER, Datex-Engstrom, Inc., Tewksbury, Mass., which is also incorporated herein by reference.

A major drawback of the previously described method of performing hollow viscus tonometry, using the device and technique briefly described above, is that it requires a specified period of time to arrive at the measurement result. Under ideal circumstances this time period is typically about one hour, but can be substantially longer. This obligatory time period is necessary because the events listed below must take place after the catheter has been placed within the body. All are required in order to arrive at a single value of tissue pH and/or tissue $pCO_2$. In the following, it is assumed that the organ in which the tonometry catheter has been placed is the stomach, although the same requirements are expected for placement in other parts of the body:

1. A measured volume of liquid must be carefully introduced through the tonometry catheter and into the balloon.

2. $CO_2$ gas dissolved in the liquid residing within the tonometry balloon must reach or approach equilibrium with the $CO_2$ gas within the hollow of the stomach.

3. Liquid must be carefully aspirated from the tonometry balloon by the tonometry catheter. For accurate measurements, it may be necessary to ensure that the liquid within the dead space volume of the catheter tube is aspirated and discarded, prior to aspirating and collecting liquid that had resided within the balloon.

4. The aspirated liquid must be sealed within a gas-tight container. Prior to sealing, any air bubbles must be expelled from the container lest they alter the level of $CO_2$ dissolved in the liquid.

5. The liquid specimen must be transported to a laboratory or location where assay instruments are available to measure the level or partial pressure of $CO_2$ gas within the liquid specimen.

6. The aspirated liquid must be assayed for the level or partial pressure of $CO_2$ gas within the liquid specimen. A skilled laboratory technician is required to perform the laboratory analysis that measures the level of $CO_2$ dissolved in the liquid specimen.

7. If insufficient time was allowed for complete equilibration while the liquid was within the balloon (typically less than about 90 minutes), the result of the $CO_2$ assay must be mathematically adjusted to obtain an estimate of the steady-state, equilibrium value. Even if the elapsed time was sufficient for complete equilibration, a mathematical adjustment is still required to account for the expected gradient between the level or partial pressure of $CO_2$ external to the balloon and the level or partial pressure of $CO_2$ dissolved in the liquid within the balloon.

8. Tissue pH must be mathematically derived from the adjusted value of the level or partial pressure of $CO_2$ dissolved in the liquid using the Henderson-Hasselbalch equation or a modification thereof.

The obligatory time for completing the above steps limits the frequency of the measurements, and in some cases makes repeated measurements within a certain time frame impossible or impractical. In addition, each of the steps must be carried out by personnel specifically trained and skilled in the above techniques, and the techniques are cumbersome to perform.

The elapsed time between filling the tonometry balloon with liquid and aspirating the liquid must be accurately determined so that the steady-state value of $CO_2$ within the balloon liquid can be accurately estimated from the measured value of $CO_2$ within the balloon liquid. Certain $CO_2$ analyzers that are commonly used in clinical laboratories have been shown to yield erroneous $CO_2$ assay results when used to measure $pCO_2$ in aspirated liquid specimens obtained from standard tonometry catheters. (See, e.g., Riddington et al., "Potential Hazards In Estimation Of Gastric Intramucosal pH", 340 *Lancet* 547 (1992); Takala et al., "Saline $PCO_2$ Is An Important Source Of Error In The Assessment Of Gastric Intramucosal pH", 22 *Crit. Care Med.* 1877–79 (1994)). Still further, the mathematics involved entail another level of understanding and training necessary to correctly obtain the final measurement value of tissue pH. This calculation generally requires the use of a calculating aid such as an electronic calculator or computer.

Besides the cumbersome sequence of techniques and the obligatory time needed to arrive at measurements of tissue pH, determination of tissue pH by this means at best provides only intermittent measurements, each isolated to a single point in time usually separated by a matter of hours. The existing art does not allow for a means of providing continuous measurements of tissue $pCO_2$ or tissue pH.

DISCLOSURE OF THE INVENTION

It is an object of the present invention to provide a method and system for determining tissue $pCO_2$ and pH which provides a continuous measurement of $pCO_2$ and pH, as well as the directional trend and rate of change of $pCO_2$ and pH.

It is an object of the present invention to provide a method and system for determining tissue $pCO_2$ and pH that shortens the time involved in the analysis.

It is an object of the present invention to provide a method and system for determining tissue $pCO_2$ and pH which eliminates the need for handling liquid specimens aspirated from a catheter located inside the body.

It is an object of the present invention to provide a method and system for determining tissue $pCO_2$ and/or tissue pH which eliminates the need for performing $CO_2$ analysis as a separate assay using a separate instrument or analyzer that is not part of the tonometry device and that may be located physically distant from the tonometry device.

It is an object of the present invention to provide a method and system for determining tissue $pCO_2$ and pH that eliminates the necessity of having skilled personnel carry out a cumbersome sequence of techniques.

It is an object of the present invention to provide a method and system for determining tissue $pCO_2$ and pH which reduces error.

Accordingly, an apparatus and method were developed to allow continuous measurement of tissue $pCO_2$ and pH using capnometric recirculating gas tonometry (CRGT).

A first embodiment of the CRGT system, termed intracorporeal CRGT, utilizes a tonometry catheter which comprises an elongate flexible tube having a proximal extracorporeal end and a distal intracorporeal end. The distal end of the tube has a distensible, inflatable, gas-permeable tonometry vessel which is filled with a gas. The distal end also has an egress orifice through which gas may flow from the tube and enter the vessel, an ingress orifice through which the gas may exit the vessel and enter the tube, an egress lumen with a distal end and a proximal end, the distal end being in communication with the egress orifice, and an ingress lumen with a distal end and a proximal end, the distal end being in communication with the ingress orifice. The proximal end of the tube has means for propelling gas into the vessel, means for continuously quantifying the level of $CO_2$ gas exiting the vessel, and a hollow connecting member linking the propelling and quantifying means to define with the vessel, the ingress lumen, and the egress lumen a closed circuit through which the gas may continuously recirculate under a relatively constant pressure, thereby resulting in a substantially error-free, stable reading.

This continuation-in-part application discloses a second embodiment of the continuous CRGT monitoring system, termed extracorporeal CRGT, in which the tonometry catheter apparatus comprises an elongate flexible tube having a proximal end and a distal end. The distal end of the tube has an ingress orifice through which a gas-containing fluid may enter the tube, an egress orifice through which the fluid may exit the tube, an ingress lumen with a distal end and a proximal end, the distal end being in communication with the ingress orifice, and an egress lumen with a distal end and a proximal end, the distal end being in communication with the egress orifice. A first hollow member links the proximal end of the ingress lumen and the proximal end of the egress lumen to define a sampling circuit through which the fluid may continuously recirculate. A second hollow member which is filled with a gas defines a closed analyzing circuit through which the gas may continuously recirculate. A gas-permeable interface links a segment of the sampling circuit with a segment of the analyzing circuit such that gas may pass therebetween, and a sensor in communication with the analyzing circuit continuously quantifies the level of gas contained within the analyzing circuit.

The above objects and other objects, features, and advantages of the present invention are more readily understood from a review of the attached drawings and the accompanying specification and claims.

BEST MODES FOR CARRYING OUT THE INVENTION

We have developed and tested an apparatus and method to allow continuous measurement of tissue $pCO_2$ and/or pH using capnometric recirculating gas tonometry (CRGT).

A. The Intracorporeal CRGT System

Figure 1:
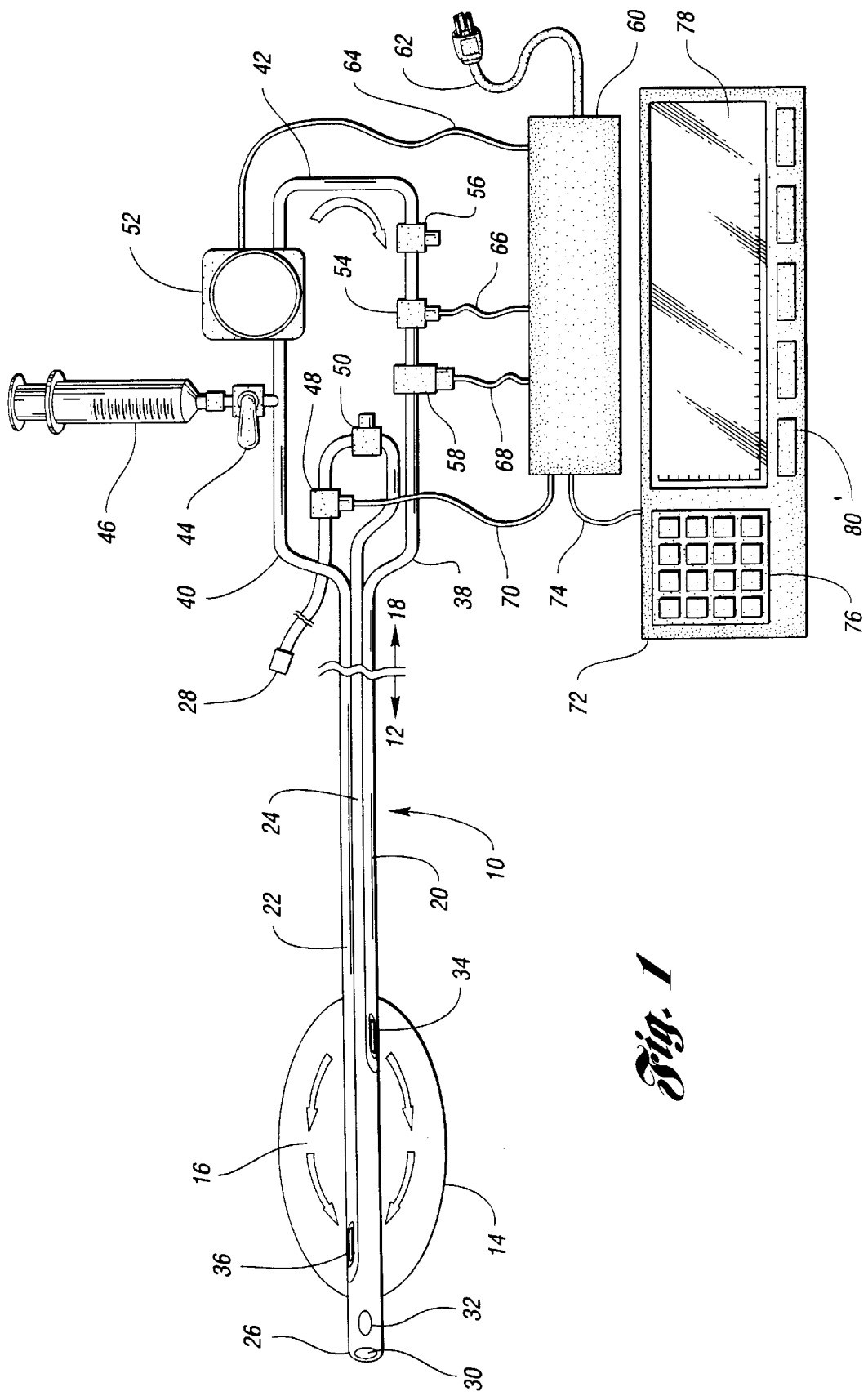
FIG. 1 is a schematic diagram of the intracorporeal CRGT system.

The intracorporeal CRGT system is depicted in FIG. 1. The tonometry catheter 10 comprises an elongate, flexible, relatively non-compliant, multilumen tube. The tube itself and the septa that separate its lumens are constructed from a material that is effectively impermeable to $CO_2$ gas, such as polyvinyl chloride (PVC) plastic. Catheter 10 has a distal, intracorporeal end 12 which is placed within an organ or tissue of a patient's body by introduction through a body orifice, such as the nose, mouth, or rectum. Catheter distal end 12 has a distensible, inflatable, gas-permeable tonometry vessel 14 situated adjacent thereto. Vessel 14 defines a confined vessel space 16 surrounding catheter distal end 12, which is filled with a gas. Catheter 10 has a proximal, extracorporeal end 18 which lies outside the body partially within an instrumentation case located at the patient's bedside.

Catheter 10 contains three internal lumens, or channels. A "pressure", or egress lumen 20 is used to convey gas to vessel 14 from catheter proximal end 18. A "vacuum", or ingress lumen 22 is used to convey gas from vessel 14 to catheter proximal end 18. In addition to egress lumen 20 and ingress lumen 22, a third, auxiliary lumen may optionally be incorporated within catheter 10. This auxiliary lumen is herein referred to as the safety pressure relief lumen 24.

Safety pressure relief lumen 24 has a distal end 26 and a proximal end 28. Distal end 26 opens into one or several orifices at catheter distal end 12. A distal end orifice 30 may be located at the distal tip of catheter 10. In addition, one or more additional distal side orifices 32 may be provided along the side of catheter 10 near its distal tip. Distal side orifices 32 are provided to obviate occlusion of all safety pressure relief lumen orifices by contact with tissue during a procedure such as aspiration. None of the orifices of safety pressure relief lumen 24 communicate with vessel space 16, with egress lumen 20, or with ingress lumen 22.

In use, proximal end 28 of safety pressure relief lumen 24 may be sealed with a clamping device or otherwise be occluded. Alternatively, proximal end 28 may be utilized for a variety of purposes that conventionally employ a standard nasogastric tube. These may include connection of proximal end 28 to a suction pump for aspirating liquid or gas from an organ or tissue as a diagnostic or therapeutic maneuver, or connection to a syringe, infusion pump, or other delivery system for introducing drugs or liquid nutrients into a tissue or organ.

Vessel 14, which may be configured as an inflatable balloon, is constructed from a silicone elastomer or other membranous material that is effectively permeable to $CO_2$ gas, but effectively impermeable to liquid. Gas is pumped from egress lumen 20 into vessel space 16 by way of an egress orifice 34 provided in catheter 10. Correspondingly, gas within vessel space 16 is aspirated through ingress lumen 22 by way of an ingress orifice 36 provided in catheter 10. Open arrows within vessel space 16 indicate the flow of gas from egress lumen 20 via egress orifice 34 to ingress lumen 22 via ingress orifice 36. It should be noted that catheter 10 would work equally well if the direction of gas flow were opposite to that depicted. Accordingly, ingress orifice 36 could be upstream of egress orifice 34, or the direction of gas flow could be reversed.

Preferably, egress orifice 34 and ingress orifice 36 are located on opposite sides of vessel 14, and the spacing between egress orifice 34 and ingress orifice 36 is maximized. Such a configuration minimizes the shunting of gas flow directly from egress orifice 34 to ingress orifice 36, which would impair the speed of equilibration of gas composition. In addition, in the preferred embodiment, the diameter of ingress orifice 36 is larger than the diameter of egress orifice 34, and ingress lumen 22 is larger than egress lumen 20. This design facilitates gas leaving vessel 14 and at the same time relatively impedes the influx of gas into vessel 14, so as to prevent the overdistention and potential rupture of vessel 14. Egress orifice 34 may optionally consist of multiple orifices located along catheter distal end 12 and opening into egress lumen 20. Ingress orifice 36 may likewise consist of multiple orifices located along catheter distal end 12 and opening into ingress lumen 22. Multiple orifices can serve to decrease the chance of occlusion in the event that one or more orifices are positioned against the membrane of vessel 14 or become occluded by condensation.

At catheter proximal end 18, egress lumen 20 and ingress lumen 22 are separated from the three-lumen portion of catheter 10 at regions 38 and 40, respectively, and are joined by a hollow connecting member 42 to form a closed circuit 22-42-20. Connecting member 42 is constructed from a material that is effectively impermeable to $CO_2$ gas. Along connecting member 42 may lie a stopcock 44 and an attached syringe 46. Syringe 46, or an alternative pressurizing device, is used to introduce additional gas into circuit 22-42-20 so as to increase the pressure within the circuit and effect distension or inflation of vessel 14 during system initialization. Syringe 46 or the alternative pressurizing device may be manually operated by the operator, or automatically operated using a syringe pump or other actuator. Stopcock 44 may be closed once vessel 14 is inflated in order to trap the introduced gas within circuit 22-42-20, thus maintaining a closed recirculating gas circuit during system operation. Stopcock 44 and syringe 46 may also be used to aspirate trapped gas from circuit 22-42-20, thereby deflating the distended vessel 14.

There are several advantages realized by employing an inflatable vessel 14. Insertion of catheter 10 into a body orifice may be accomplished when vessel 14 is in the deflated state, thereby minimizing the size or diameter of catheter distal end 12 and facilitating its insertion. Once vessel 14 is positioned at the desired location within the body, vessel 14 can be inflated and assume a larger surface area than would be possible using a noninflatable vessel. The increased surface area accelerates the equilibration of gas concentrations across the membrane of vessel 14, allowing faster, more accurate measurements than if the surface area was fixed. In addition, injecting additional gas stretches the membrane of vessel 14, decreasing its thickness and thereby minimizing its resistance to diffusion of gases.

Whether or not an inflatable vessel is used, using syringe 46 to inject additional gas into circuit 22-42-20 increases the pressure within the circuit, and thereby increases the rate of diffusion of gas molecules across the wall of vessel 14 allowing faster equilibration. By opening stopcock 44 after initial pressurization of the system, but locking the piston of syringe 46 in place, the gas within syringe 46 will be of identical composition as the gas within circuit 22-42-20. Thus, injection of additional gas from syringe 46 during operation will not alter the composition of the gas mixture within circuit 22-42-20, which would impair the accuracy of the intended measurements. Additional gas may also be injected by way of syringe 46 during operation for the purpose of replacing any volume loss from catheter 10 which might develop during operation, such that the inflation volume of vessel 14 can be maintained. Additional gas may also be injected by syringe 46 during operation for the purpose of maintaining constant pressure within circuit 22-42-20. In order to counter any loss of pressure that might develop over time, and to counter the effect of this loss on the partial pressure of gases within circuit 22-42-20. Similarly, a volume of gas may be aspirated from circuit 22-42-20 by way of syringe 46 during operation in order to counter any rise in pressure that might develop due to pressure applied to the tubing or components comprising circuit 22-42-20 or vessel 14, and to counter the effect of this pressure rise on the partial pressure of gases within circuit 22-42-20.

Prior to placement of catheter 10 into the patient's body, circuit 22-42-20 may comprise nontoxic gases such as helium, $CO_2$, nitrogen, or a mixture of any of these gases, with or without air. The preferred method utilizes an initial gas mixture containing a physiologic concentration of $CO_2$, approximately 5%, to minimize the initial $CO_2$ gradient across the wall of vessel 14, with the remainder of the gas being helium. Since helium diffuses more rapidly than denser gases and air, it may be used in combination with $CO_2$ to minimize the time to achieve equilibration of gas concentration within and external to vessel 14. Use of this mixture allows accurate measurements to be obtained more rapidly than if air, alternative gas mixtures, or aqueous solutions are used.

A pressure transducer 48, or other means of monitoring pressure such as an electronic strain gauge transducer, pressure activated electrical switch, pressure gauge, or other pressure activated mechanical, electrical, or electromechanical device, may optionally be intercalated within or attached to proximal end 28 of safety pressure relief lumen 24. Pressure transducer 48 is used to sense and quantify the pressure within safety pressure relief lumen 24 and serve as a means of indicating an abnormally high pressure within the tissue or organ that may be due to a device malfunction.

Correspondingly, a pressure relief valve 50 may optionally be intercalated within or attached to proximal end 28 of safety pressure relief lumen 24. Pressure relief valve 50 allows excessive tissue or organ pressure to be vented from the tissue or organ to the atmosphere, and therefore acts as a safety device in the event of a malfunction such as the occlusion of distal end 28 of safety pressure relief lumen 24. The pressure at which pressure relief valve 50 opens is such that valve 50 is unlikely to open at pressures that can occur under normal physiologic conditions, but such that it will open if a higher degree of tissue or organ pressure should occur. Pressure relief valve 50 may be constructed so as to mechanically change its shape specifically to provide a visual indication that the pressure has been exceeded. Alternatively, pressure transducer 48 may provide a signal when pressure relief valve 50 is activated, thus alerting the operator that a malfunction may have occurred.

A pump 52 is provided as a means for propelling gas in one direction through circuit 22-42-20. Pump 52 may consist of a peristaltic pump, roller pump, diaphragm pump, impeller pump, or other type of pump. The direction of gas flow is illustrated by the open arrow shown immediately to the right and below pump 52. However, the invention would function equally well if the direction of flow were reversed. Pump 52 should be suitable for propelling gas through hollow tubes at any rate of flow, including zero flow. At zero flow, movement of gas within the circuit is effected by diffusion rather than convection.

The rate of $CO_2$ equilibration across a $CO_2$-permeable membrane is proportional to the rate of molecular diffusion and the degree of convective motion of molecules in the vicinity of the membrane. In conventional hollow viscus tonometry using catheters tipped with fluid-filled vessels, no convective molecular motion occurs on either side of the vessel during the equilibration process, instead, molecular diffusion alone is relied upon to effect equilibration. In the intracorporeal CRGT system, pump 52 expedites equilibration by providing convective motion of molecules within vessel space 16, potentially increasing the responsiveness and sensitivity of the measurement of tissue $pCO_2$ and pH.

By employing a propelling pump that does not come into direct contact with the gas circulating inside circuit 22-42-20, the CRGT system has the advantage of preventing microbial cross-contamination when the device is used in different human subjects. In prior art systems, if vessel 14 were to rupture, body fluids from the patient would enter the lumen of catheter 10 and be aspirated by pump 52, thereby causing contamination. The contaminated pump could not be used on another patient without subjecting that patient to the risk of infectious diseases that are transmitted by body fluids, such as the human immunodeficiency virus (HIV), hepatitis viruses, tuberculosis, and others. In the system of the present invention, pump 52 operates by sequentially squeezing the exterior surface of flexible circuit 22-42-20 such that all structures of pump 52 are external to circuit 22-42-20 and cannot contact the lumen of circuit 22-42-20 or its contents. Therefore, catheter 10 can be made disposable without the necessity of employing a disposable pump 52, or catheter 10 can be sterilized and reused without having to sterilize pump 52 between use on different patients.

Alternatively, pump 52 may operate to facilitate diffusion of gas molecules through circuit 22-42-20. This can be accomplished by employing a piston pump or diaphragm pump having a small stroke and operating volume at a relatively high frequency. To minimize the effects of pressure fluctuations on $CO_2$ measurement, pump 52 may operate intermittently, wherein measurements are made while pump 52 is not operating, or pump 52 may operate at a high frequency and small stroke volume so as to minimally affect pressure within circuit 22-42-20. $CO_2$ measurements may be corrected for the effects of pressure fluctuations as measured by a pressure transducer 54 within circuit 22-42-20. The intracorporeal CRGT system may operate with no propelling means whatsoever; however, sensitivity and time responsiveness of the system will be expected to substantially decrease.

Another means of enhancing diffusion through circuit 22-42-20 is to apply a high-speed vibrator over the circuit at any point along its length. The vibrations will be transmitted through the wall of circuit 22-42-20, vibrating the gas molecules contained therein and thus enhancing their diffusion rate. Heating circuit 22-42-20 would have the same effect, but has practical limitations since excess applied heat could be transmitted to the body of the subject under study.

For sensing and quantifying the pressure within the lumen of catheter 10, pressure transducer 54 is provided anywhere in circuit 22-42-20, but preferably in close proximity to a $CO_2$ sensor 58 and downstream of pump 52. Pressure transducer 54 serves to indicate an abnormal increase in pressure within circuit 22-42-20 that may be due to overpressurization or device malfunction, and serves to indicate when there is low pressure within circuit 22-42-20, which may reflect inadequate pressurization or a loss of integrity. In addition, pressure transducer 54 serves to indicate whether vessel 14 is inflated or deflated if an inflatable vessel is used. The output of pressure transducer 54 may be used to control operation of pump 52, for example, by turning pump 52 off if the pressure exceeds a certain value. If a syringe pump or other actuator is employed for automatically pressurizing and/or depressurizing circuit 22-42-20, the volume of gas injected or aspirated will be controlled by an electronic circuit, represented by box 60, and regulated by pressure transducer 54. Electronic circuit 60 may thus adjust the volume introduced into or removed from circuit 22-42-20 by syringe 46 in order to maintain an optimal, and relatively constant, pressure level within circuit 22-42-20.

Optionally, a pressure relief valve 56 may be intercalated within circuit 22-42-20 anywhere downstream of pump 52. Pressure relief valve 56 acts as a safety device in event of a system malfunction that results in gas exiting circuit 22-42-20, entering the patient's body, and causing a gaseous distention of the tissue or organ which might result in bodily harm. For example, this situation could prevail if the following events occurred:

1. Vessel 14 ruptures, allowing gas from circuit 22-42-20 to enter the tissue or organ;

2. A portion of ingress lumen 22 becomes occluded at a point between its distal end and the point of connection with pump 52;

3. Ingress lumen 22 ruptures or otherwise becomes open to the atmosphere between pump 52 and the point of the aforementioned occlusion;

4. Safety pressure relief lumen 24, or the proximal 28 or distal 30 and 32 openings of safety pressure relief lumen 24 all become occluded, or if the lumen or openings are of insufficient caliber to vent gas pumped into the organ or tissue surrounding vessel 14, or if these openings are not in proximity or communication with the gas pumped into the organ or tissue; or 5. Pressure relief valve 50 malfunctions or becomes occluded.

Each of the above-listed conditions may be effectively ameliorated by valve 56. Although pressure relief valve 56 is designed similarly to pressure relief valve 50, pressure relief valve 56 opens at a pressure that exceeds the normal working pressure of circuit 22-42-20. This pressure threshold may be higher than the threshold used by pressure relief valve 50.

Sensor 58 may be provided at any point in circuit 22-42-20 to measure the level, percentage, concentration, or partial pressure of $CO_2$ gas within circuit 22-42-20 and hence within vessel space 16. Sensor 58 may include any type of non-destructive $CO_2$ sensor, such as an infrared spectroscopic $CO_2$ sensor, a spectrophotometric sensor, an optical dye sensor, a polarographic electrode sensor, a fluorescent optode $CO_2$ sensor, or other nondestructive $CO_2$ gas analysis device that can be used for gas mixtures within a closed system. The final output of sensor 58 consists of an electrical signal that is proportional, with respect to voltage, current, frequency, phase or other electrical property, to the level, percentage, concentration, or partial pressure of $CO_2$ within circuit 22-42-20. $CO_2$ measurements may be corrected for the effects of pressure fluctuations as measured by pressure transducer 54 within circuit 22-42-20.

Alternatively, to provide a means for measuring and quantifying the level, percentage, concentration, or partial pressure of $CO_2$ gas within circuit 22-42-20, a capnometer, capnograph, or other similar device may be provided. Such a device is generally electrically or optically connected to sensor 58, or is an integral part of sensor 58. Preferably, the $CO_2$ measurement device is a mainstream capnograph. Alternatively, a sidestream capnograph may be used. Preferably, sensor 58 communicates with an electronic circuit 60 which provides a means for controlling the capnometer display or capnograph, and triggers a signaling device which emits an audible or generates a visual alarm when certain values are exceeded or fall below pre-selected values.

Electronic circuit 60 includes a power supply, gas analysis electronics, an audible alarm device, and a microprocessor for performing calculations, controlling pump 52, and driving a display screen if one is used. Circuit 60 is powered via an electrical power cable 62 and may also be battery operated. Another electrical cable 64 provides power to pump 52. Cables 66 and 68, respectively, are cables that connect circuit 60 to pressure transducer 54 and sensor 58. A cable 70 connects pressure transducer 48 associated with safety pressure relief lumen 24 to electronic circuit 60.

A control and display panel is represented by reference numeral 72. An electrical cable 74 connects panel 72 to electronic circuit 60. Panel 72 provides a means for entering the value of blood, serum, or plasma bicarbonate concentration, critical value alarm limits, and other information by a push-button or pressure-sensitive keyboard 76, key pad, push buttons, electrical or electronic switches, or other input devices. Additionally, panel 72 may provide a display means 78 for displaying the results of values derived from any one or combination of the following in digital, analog, graphical, or other form using lights, light emitting diodes, a cathode ray tube, liquid crystal display, a printer, or other means of display: the blood, serum or plasma bicarbonate concentration, other blood test values (such as blood pH or $pCO_2$), other physiological measurements (such as end-tidal $pCO_2$ of expired gas), pressures measured by pressure transducers 48 and 54, speed or flow rate of pump 52, and position of any actuator used to automatically operate syringe 46, and the measured value of the level, percentage, concentration, and partial pressure of $CO_2$ gas within circuit 22-42-20. Ideally, panel 72 includes a means, such as function switches 80, for selecting the configuration of the displayed results. Display means 78 may also provide textual information regarding the operation of the invention, indicate alarm conditions, and prompt the user as to system operation, such as how to input information by way of keyboard 76 or function switches 80. The CRGT system can also be provided with electronic circuitry to automatically perform the calculation of tissue pH or other derived values and display these values in similar fashion.

As mentioned above, tissue pH, also known as intracellular pH, $pH_i$ or the negative logarithm of intracellular hydrogen ion activity, may be calculated from $pCO_2$ using the Henderson-Hasselbalch equation (Henderson L. J., "The Theory Of Neutrality Regulation In The Animal Organism," 21 Am. J. Physiol. 427 (1908); Hasselbalch K. A., "Die Berechnung der Wasserstoffzahl des Blutes aus der freien und gebundenen Kohlensäure desselben, und dieSauerstoffbindung des Blutes als Funktion der Wasserstoffzahl," 78 Biochem. Z. 112 (1916); and Kruse J. A., "Relationship Between The Apparent Dissociation Constant Of Blood Carbonic Acid And Severity Of Illness," 114 J. Lab. Clin. Med. 568–574 (1989)) as follows:

$$pH_i = pK' + \log_{10} \frac{[HCO_3^-]}{s \times pCO_2}$$

where "pK" is the apparent first dissociation constant of carbonic acid, a constant equal to approximately 6.1; "s" is the solubility coefficient, also known as Bunsen's coefficient, of $CO_2$ gas in physiological solution, a constant approximately equal to 0.03 mmol/L per torr at 37° C.; and "$[HCO_3^-]$" is the molar concentration of bicarbonate inside the cells of the tissue or organ. The latter is held to be equal to or approximated by the molar concentration of bicarbonate in blood, plasma, or serum. Thus, if arterial bicarbonate concentration is known, tissue pH ($pH_i$) can be determined mathematically using the Henderson-Hasselbalch equation and the value of tissue $pCO_2$ determined by the intracorporeal CRGT system.

The intracorporeal CRGT system has been described in terms of its capability for $CO_2$ measurement. In general, an intracorporeal recirculating gas tonometry system as described above can also be used to determine the concentration of any gas that may be contained within the tissue of the body. This may be accomplished by ensuring that vessel 14 is permeable to the particular gas to be measured, and that sensor 58 will detect and quantify the level of the particular gas to be measured.

B. Experimental Results for the Intracorporeal CRGT System

Performance of the intracorporeal CRGT system of the present invention was validated in vivo in seven anesthetized, mechanically ventilated dogs weighing 15 to 22 kg. For each experiment, the distal end of catheter 10 was placed in the animal's stomach via the mouth and connected to the extracorporeal instrument portion of the CRGT apparatus. A second prior art catheter was also placed in the animal's stomach and saline solution was instilled into its chamber. Thus, the intracorporeal CRGT system was used to continuously monitor gastric intramucosal $pCO_2$ and pH. The purpose of using the conventional, intermittent tonometry catheter was to obtain an independent measurement of gastric intramucosal $pCO_2$ and pH for comparison. Within the time frame of these experiments, the conventional tonometry catheters only allow a single measurement to be made, and therefore do not allow continuous monitoring.

Using the intracorporeal CRGT system, $pCO_2$ was recorded at 5-minute intervals for 30 minutes. At the end of the 30-minute partial equilibration period, the saline solution was aspirated from the conventional tonometry catheter and analyzed for $pCO_2$ using a laboratory blood gas analyzer (model ABL-2; Radiometer, Inc.; Westlake, Ohio). Using the equation:

$$[HCO_3^-] = s \times pCO_2 \times 10^{(pH-pK)},$$

the same instrument was used to determine bicarbonate concentration from an arterial blood specimen of each animal (Kruse et al., "Relationship Between The Apparent Dissociation Constant Of Blood Carbonic Acid And Severity Of Illness," 114 J. Lab. Clin. Med. 568–574 (1989)).

The $pCO_2$ value obtained at 30 minutes by the intracorporeal CRGT system was compared to the $pCO_2$ value obtained by laboratory analysis of the saline from the conventional catheter. Gastric intramucosal pH was calculated from the $pCO_2$ values obtained by intracorporeal CRGT and by conventional intermittent tonometry extrapolated to steady state levels, the arterial blood bicarbonate concentration, the pK' of carbonic acid in blood, the solubility coefficient of $CO_2$ gas in plasma, and the Henderson-Hasselbalch equation.

$pCO_2$ determined by intracorporeal CRGT rose from zero to a near plateau by the end of the 30-minute period. Using a repeated measures analysis of variance, Fisher's PLSD multiple comparison statistic, and a two-tailed $\alpha$ probability level of 0.05, the 30-minute $pCO_2$ values obtained by intracorporeal CRGT were not significantly different from the values obtained at 25 minutes, statistically corroborating the plateau. Using a Student's paired t test and a two-tailed a probability level of 0.05, the $pCO_2$ values obtained by intracorporeal CRGT at 30 minutes were not significantly different from the $pCO_2$ values obtained at 30 minutes by conventional intermittent tonometry. This indicates agreement with measurements obtained using the prior art.

Similarly, the pH values derived by intracorporeal CRGT at 30 minutes were in statistical agreement with the pH values obtained at 30 minutes by conventional intermittent tonometry. Related animal experiments subsequently performed under conditions of hypoxemia (Guzman and Kruse, "Development and Validation of a Technique for Continuous Monitoring of Gastric Intramucosal pH", 153 AM. J. RESP. CRIT. CARE MED., 694–700 (1996)), hemorrhage (Guzman and Kruse, "Continuous Assessment of Gastric Intramucosal $PCO_2$ and pH in Hemorrhagic Shock Using Continuous Recirculating Gas Tonometry", 25 CRIT. CARE MED., 533–537 (1997); and Guzman and Kruse, "Gastric Intramucosal $PCO_2$ as a Quantitative Indicator of the Degree of Acute Hemorrhage", J. CRIT. CARE (in press)), and endotoxemia (Guzman et al, "Gastric and Esophageal Intramucosal $PCO_2$ ($PiCO_2$) During Endotoxemia: Assessment of Raw $PiCO_2$ vs $PCO_2$ Gradients as Indicators of Hypoperfusion in a Canine Model of Septic Shock" CHEST (in press)) have shown either similar agreement between the two methods, or have shown that intracorporeal CRGT can detect statistically significant changes in gastrointestinal intramucosal pH and/or $PCO_2$ more quickly and with greater sensitivity and responsiveness than the prior art method. These studies have also shown that intracorporeal CRFT can identify changes in gastrointestinal intramucosal $pCO_2$ and/or pH within minutes of experimentally induced tissue hypoxia. In vitro comparisons of intracorporeal CRGT provides measurements of $pCO_2$ that are either equal to that obtained by the prior art method (Guzman and Kruse, "Development and Validation of a Technique for Continuous Monitoring of Gastric Intramucosal pH," 153 AM. J. RESP. CRIT. CARE MED., 694–700 (1996)), or are superior to measurements obtained by the prior art method with respect to accuracy and precision obtained by the prior art method with respect to accuracy and precision (Guzman and Kruse, "Accuracy and Precision of Two Methods for Measuring Gastric Intramucosal $PCO_2$ ($PiCO_2$). Comparison Between Standard Saline Tonometry (SST) and Capnometric Recirculating Gas Tonometry (CRGT)", 110 (suppl) CHEST 74S (1996)).

C. The Extracorporeal CRGT System

The above describes an intracorporeal CRGT system and method in which the tonometric equilibration of gas tension or concentration occurs across a vessel membrane residing within the body. An alternative system and method (FIGS. 2–6) is extracorporeal CRGT, in which the tonometric equilibration of gas concentration occurs across a membrane device residing outside the body.

Figure 2:
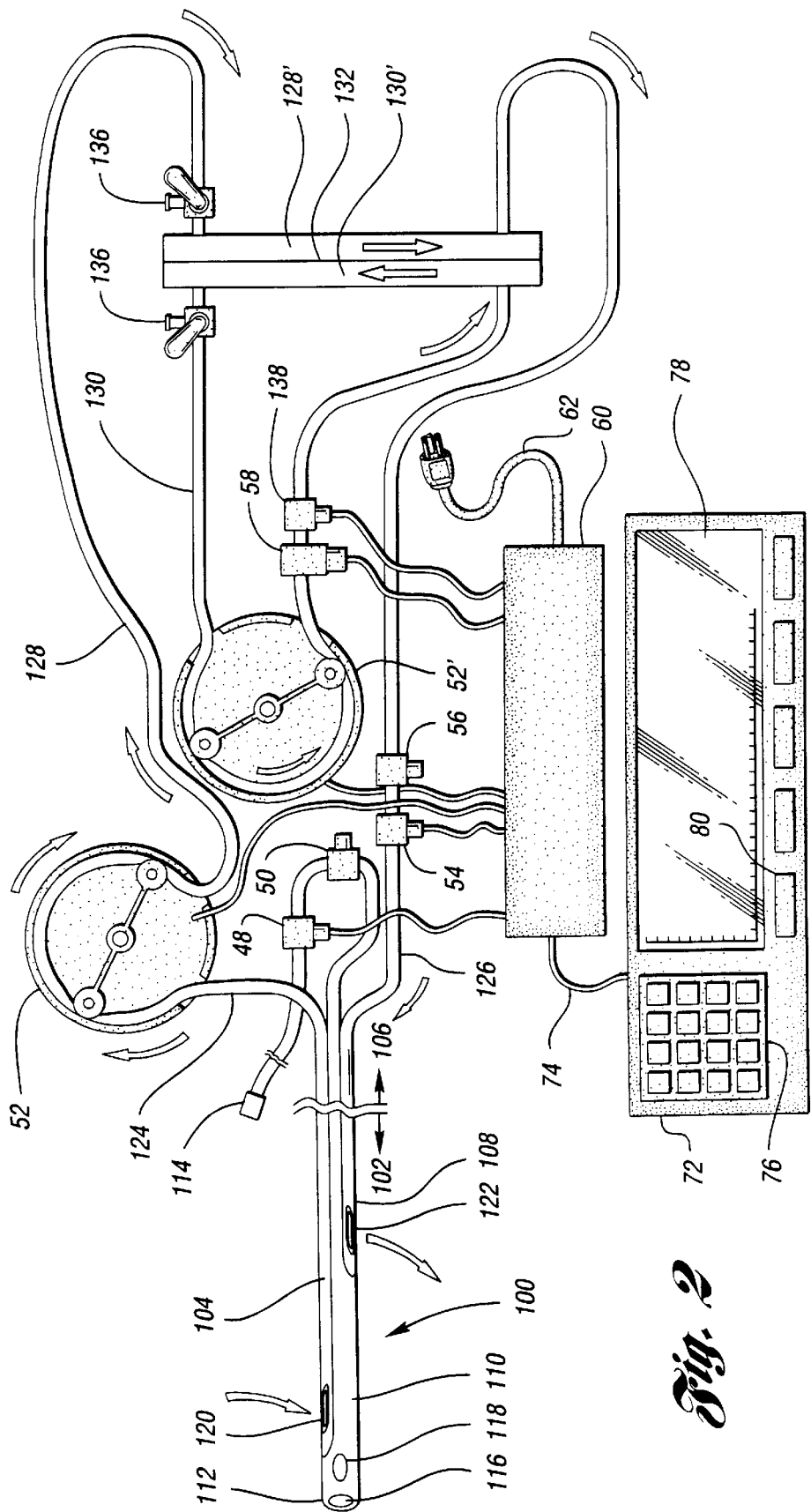
FIG. 2 is a schematic diagram of the extracorporeal CRGT system of the present invention.

The extracorporeal CRGT system of the present invention is initially depicted in FIG. 2. Instead of the specialized tonometry catheter 10 used in the intracorporeal CRGT system, a standard, multilumen catheter 100 is employed in the extracorporeal CRGT system. Any multilumen catheter that can function to remove contents from a hollow viscus or instill fluids, nutrients, or drugs into a hollow viscus, such as a conventional nasogastric catheter, could be used directly or adapted for this application. Catheter 100 is constructed from a material that is effectively impermeable to $CO_2$ gas, such as polyvinyl chloride (PVC) plastic. Catheter 100 has a distal, intracorporeal end 102 which is placed within an organ or tissue of a patient's body by introduction through a body orifice. Since extracorporeal CRGT does not require a vessel on catheter distal end 102, the caliber of catheter distal end 102 can be smaller. As a result, insertion may be accomplished with potentially less discomfort to the patient, without sacrificing efficiency, sensitivity, or responsiveness of the measurements.

Catheter 100 preferably contains at least two internal lumens, or channels. A "vacuum", or ingress lumen 104 is used to convey fluid, defined herein as a mixture of gas and liquid, sampled from the hollow organ to a proximal, extracorporeal end 106 of catheter 100. A "pressure", or egress lumen 108 is used to convey fluid from catheter proximal end 106 back to the hollow organ. Lumens 104 and 108 may be arranged in either a parallel or coaxial fashion. In addition to ingress lumen 104 and egress lumen 108, a third, auxiliary lumen is preferably incorporated within catheter 100. This auxiliary lumen is herein referred to as the safety pressure relief lumen 110.

Safety pressure relief lumen 110 has a distal end 112 and a proximal end 114. Distal end 112 opens into one or several orifices at catheter distal end 102. A distal end orifice 116 may be located at the distal tip of catheter 100. In addition, one or more additional distal side orifices 118 may be provided along the side of catheter 100 near its distal tip. Distal side orifices 118 are provided to obviate occlusion of all safety pressure relief lumen orifices by contact with tissue during a procedure such as aspiration. None of the orifices provided in safety pressure relief lumen 110 communicate with ingress lumen 104 or egress lumen 108.

Fluid within the hollow organ space flows into ingress lumen 104 by way of an ingress orifice 120 provided in catheter 100, as indicated by the open arrows. Egress orifice 122 may optionally consist of multiple orifices located along catheter distal end 102 and opening into egress lumen 108. Ingress orifice 120 may likewise consist of multiple orifices located along catheter distal end 102 and opening into ingress lumen 104. Multiple orifices can serve to decrease the chance of occlusion in the event that one or more orifices are positioned against a bodily tissue or become occluded by products of digestion. Correspondingly, fluid flows from egress lumen 108 back into the hollow organ space by way of an egress orifice 122 provided in catheter 100, again indicated by open arrows. It should be noted that catheter 100 would work equally well if the direction of fluid flow were opposite to that depicted. Accordingly, ingress orifice 120 could be upstream of egress orifice 122, or the direction of fluid flow could be reversed.

Preferably, ingress orifice 120 and egress orifice 122 are located on opposite sides of catheter 100, and the spacing between ingress orifice 120 and egress orifice 122 is maximized. Such a configuration minimizes the shunting of fluid flow directly from egress orifice 122 to ingress orifice 120, which would impair the speed of equilibration of gas composition within the fluid. In the preferred embodiment, as in the intracorporeal CRGT system, the diameter of ingress orifice 120 is larger than the diameter of egress orifice 122, and the diameter of ingress lumen 104 is larger than the diameter of egress lumen 108. This design facilitates fluid leaving the hollow organ, and at the same time relatively impedes the influx of fluid into the hollow organ, allowing development of a degree of pressure within circuit 22-42-20 downstream of pump 52 and upstream of egress orifice 122, facilitating maintenance of patency of this portion of circuit 22-42-20.

In use, proximal end 114 of safety pressure relief lumen 110 may be sealed with a clamping device or otherwise be occluded. Alternatively, it may be utilized for a variety of purposes that conventionally employ a standard nasogastric tube. These may include connection of proximal end 114 to a suction pump for aspirating liquid or gas from an organ or tissue as a diagnostic or therapeutic maneuver, or connection to a syringe, infusion pump, or other delivery system for introducing drugs or liquid nutrients into a tissue or organ. A pressure sensing means, such as pressure transducer 48, and pressure relief valve 50, with characteristics as described previously, are incorporated along safety pressure relief lumen 110 for the same purposes as in the intracorporeal CRGT system.

At catheter proximal end 106, ingress lumen 104 and egress lumen 108 are separated from the three-lumen portion of catheter 100 at regions 124 and 126, respectively, and may be joined by a first hollow member 128 which is constructed from a material that is effectively impermeable to $CO_2$ gas. Ingress lumen 104, egress lumen 108, and first hollow member 128 form a sampling circuit 104-128-108 through which fluid residing within the hollow organ can be removed, circulated, and returned to the hollow organ on either an intermittent or continuous basis. A pressure sensing means, such as pressure transducer 54, and pressure relief valve 56, with characteristics as described previously, may be intercalated within sampling circuit 104-128-108 for the same purposes as in the intracorporeal CRGT system.

In the extracorporeal CRGT system, the purpose of sampling circuit 104-128-108 is to remove gas-containing fluid from a hollow organ, circulate the fluid, and return the fluid to the hollow organ. Still referring to FIG. 2, a second hollow member, constructed from a material that is effectively impermeable to $CO_2$ gas, forms an extracorporeal analyzing circuit 130 which is used to quantify the level of gas contained within fluid circulating through sampling circuit 104-128-108. Analyzing circuit 130 communicates with sampling circuit 104-128-108 through a $CO_2$-permeable interface, or membrane, 132 interposed between a segment 128' of sampling circuit 104-128-108 and a segment 130' of analyzing circuit 130. Membrane 132 is constructed from a silicone elastomer or other membranous material that is effectively permeable to $CO_2$ gas, but effectively impermeable to liquid. $CO_2$ contained in the circulating fluid will diffuse through membrane 132, causing the $CO_2$ concentration within analyzing circuit 130 to ultimately equilibrate with the $CO_2$ concentration of the hollow organ.

In the embodiment shown in FIG. 2, segments 128' and 130' are parallel to each other, and membrane 132 is interposed therebetween. Alternatively, in the embodiments of the invention depicted in FIGS. 3 and 6, segments 128' and 130' are configured in a coaxial arrangement. As shown in the cross-sectional view of FIG. 4 and the longitudinal view of FIG. 5, segment 128' is surrounded by segment 130' and separated from segment 130' by membrane 132. The junctures 134 demarcating segments 128' and 130', and the transformation between non-coaxial and coaxial configurations, are constructed in such a way that matter cannot escape from either circuit. It is also possible to reverse the coaxial arrangement such that segment 128' surrounds segment 130'.

A syringe 46 and associated stopcock 44, with characteristics as described previously, or an alternative pressurizing device, may optionally be connected to analyzing circuit 130 as a means for injecting additional gas into analyzing circuit 130 in order to increase the pressure within analyzing circuit 130 as described above for the intracorporeal CRGT system. Increased pressure within analyzing circuit 130 will facilitate diffusion across membrane 132, expediting tonometric equilibration. In the coaxial membrane embodiment shown in FIGS. 3 and 6, to coaxial portions of the two circuits may be reversed such that analyzing circuit 130 is configured as the inner lumen and sampling circuit 104-128-108 is configured as the outer lumen of the coaxial tubing. In this alternative embodiment, pressurizing analyzing circuit 130 allows for a thinner and hence more compliant membrane 132 separating the two coaxial lumens, while minimizing the potential for collapse of segment 130' due to the compliance characteristics of the membrane 132 and any static or dynamic changes in pressure within segment 128'.

Although the caliber of ingress lumen 104 and egress lumen 108 are limited to a size that will allow insertion of catheter distal end 102 within the body, the caliber of analyzing circuit 130 is not subject to such a limitation. Thus, the recirculation rate at a given pressure within analyzing circuit 130 may be increased above the recirculation rate used in sampling circuit 104-128-108, further increasing the efficiency of tonometric equilibration and enhancing the sensitivity and responsiveness of the measurements.

Prior to placement of catheter 100 into the patient's body, analyzing circuit 130 may comprise a nontoxic gas such as helium, $CO_2$, nitrogen, or a mixture of any of these gases, with or without air. For the reasons outlined for the intracorporeal CRGT system, the preferred method utilizes an initial gas mixture containing a physiologic concentration of $CO_2$, approximately 5%, to minimize the initial $CO_2$ gradient across membrane 132, with the remainder of the gas being helium. As described for the intracorporeal CRGT system, diffusion of gas molecules through membrane 132 can be further facilitated by employing a rapidly operating piston pump or a high-speed vibrator over the circuits at any point along their length.

Other factors being equal, the rate of $CO_2$ equilibration across a $CO_2$-permeable membrane is proportional to the surface area of the membrane. In conventional hollow viscus tonometry and intracorporeal CRGT, the surface area of the vessel utilized is limited by the size of the body orifice through which it is inserted or the internal dimensions of the hollow organ in which it resides. In the extracorporeal CRGT system, membrane 132 lies outside the body, and the surface area of membrane 132 is therefore unlimited. Increasing the surface area of membrane 132 potentially increases the responsiveness and sensitivity of the measurement of tissue $pCO_2$ and pH.

Conventional hollow viscus tonometry and intracorporeal CRGT both utilize vessel-tipped catheters in which the vessel is constructed from a $CO_2$-permeable membrane. Diffusion of gas molecules through the membrane is facilitated by employing as thin a membrane as is practical. However, if the membrane is too thin, it is at risk for becoming damaged and losing its integrity as it is being advanced into the body. Thinness of the vessel wall, and hence gas permeability, is also limited by the distending pressure needed to inflate the vessel without causing it to rupture. In the extracorporeal CRGT system, membrane 132 lies outside the body, and is not inserted through body orifices or passages that create friction and limit the thinness of membrane 132. Membrane 132 is also surrounded in its entirety by segments 128' and 130', thus providing additional protection from frictional or other forces during handling and operation. This allows membrane 132 to be thinner than that employed in the vessels of conventional or intracorporeal CRGT, allowing more rapid diffusion and increasing the responsiveness and sensitivity of the measurement of tissue pCO, and pH.

Figure 3:
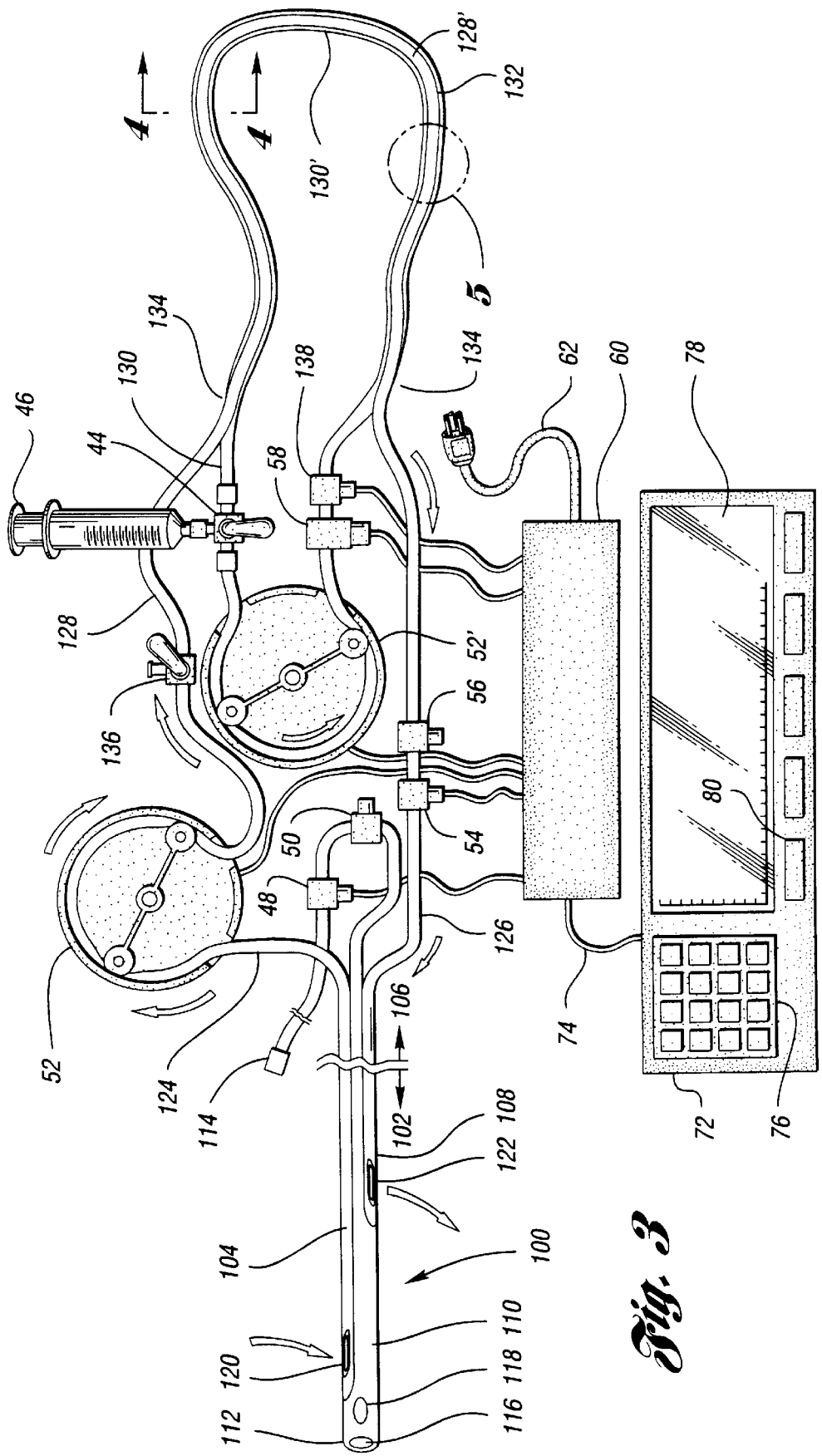
FIG. 3 is a schematic diagram of an embodiment of the extracorporeal CRGT system utilizing coaxial segments of the sampling and analyzing circuits for gas exchange.
Figure 4:
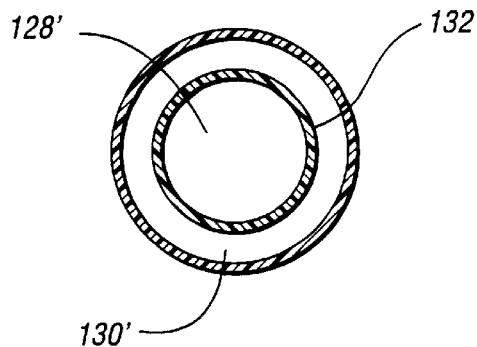
FIG. 4 is a cross-sectional view of the coaxial segments of the sampling and analyzing circuits.
Figure 7:
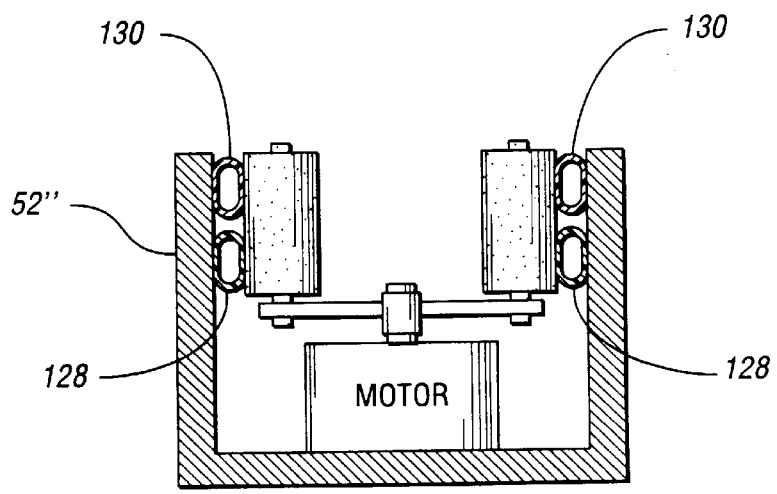
FIG. 7 is a cross-sectional view of the single pump.
Figure 6:
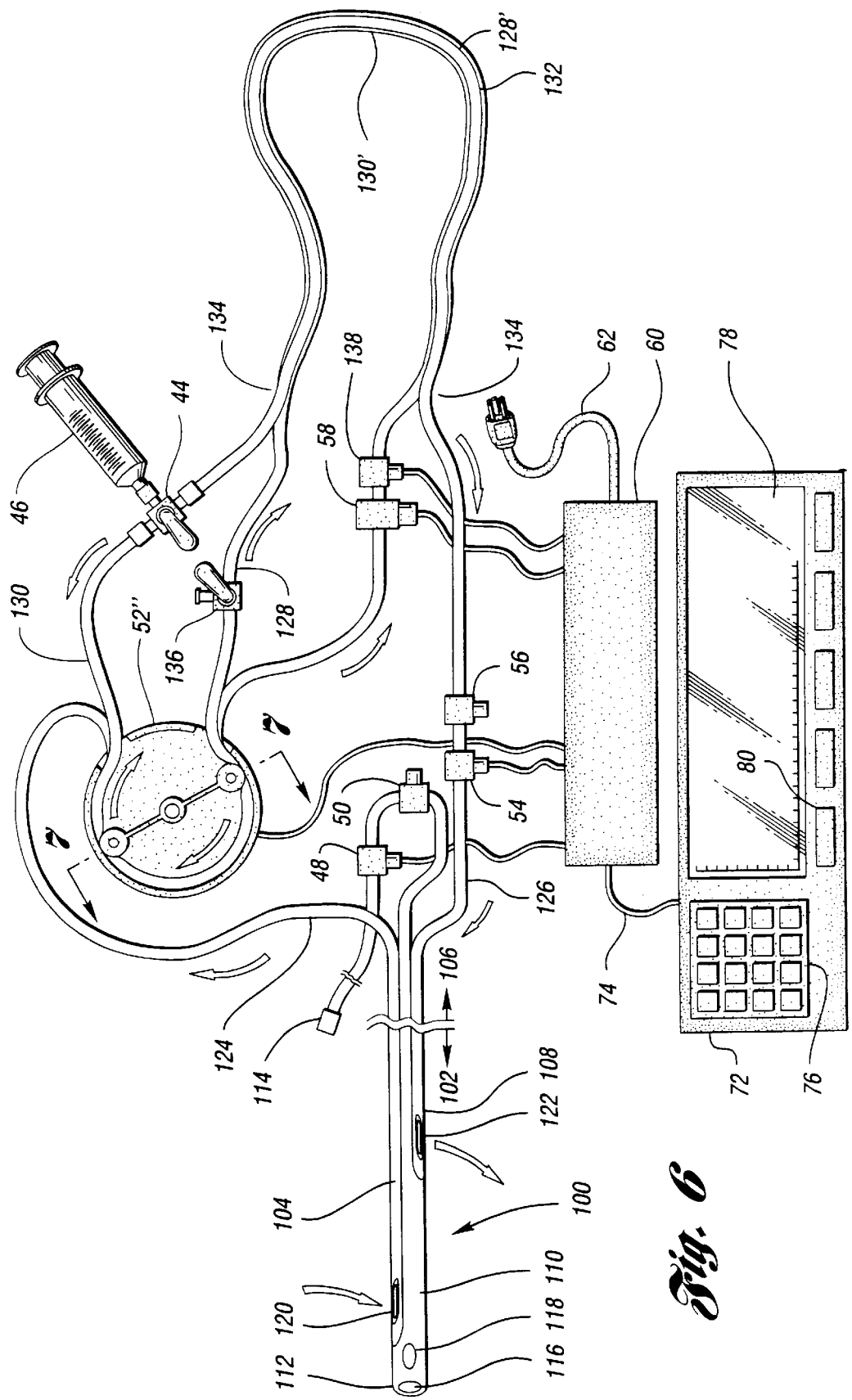
FIG. 6 is a schematic diagram of an embodiment of the extracorporeal CRGT system utilizing a single pump.

As shown in FIGS. 2 and 3, a pump 52, with characteristics as described previously, is provided as a means for propelling fluid in one direction through sampling circuit 104-128-108, either intermittently or continuously. Gas contained within analyzing circuit 130 is recirculated by a second pump 52'. In the embodiment of the invention depicted in FIG. 6, a single pump 52" is used to recirculate gas through analyzing circuit 130 and gas-containing fluid through sampling circuit 104-128-108. As shown in FIG. 7, this is accomplished by positioning a portion of first hollow member 128 of sampling circuit 104-128-108 and a portion of analyzing circuit 130 both within the pumphead of a single roller or peristaltic pump. The recirculating rate of sampling circuit 104-128-108 and analyzing circuit 130 can be controlled separately or in concert by altering the speed of pumps 52, 52', or 52", or by altering the caliber of first hollow member 128 of sampling circuit 104-128-108 and the caliber of analyzing circuit 130 where each is compressed. The extracorporeal CRGT system may operate with no propelling means whatsoever, or propelling means provided in only one circuit; however, sensitivity and time responsiveness of the system will be expected to substantially decrease.

The rate of $CO_2$ equilibration across a $CO_2$-permeable membrane is proportional to the rate of molecular diffusion and the degree of convective motion of molecules in the vicinity of the membrane. In the intracorporeal CRGT system, pump 52 expedites equilibration by providing convective motion of molecules on only one side of the membrane, within vessel space 16. In the extracorporeal CRGT system, pumps 52, 52', or 52" can be used to provide convective motion of molecules on both sides of membrane 132, further expediting the equilibration process and potentially increasing the responsiveness and sensitivity of the measurement of tissue $pCO_2$ and pH.

Figure 5:
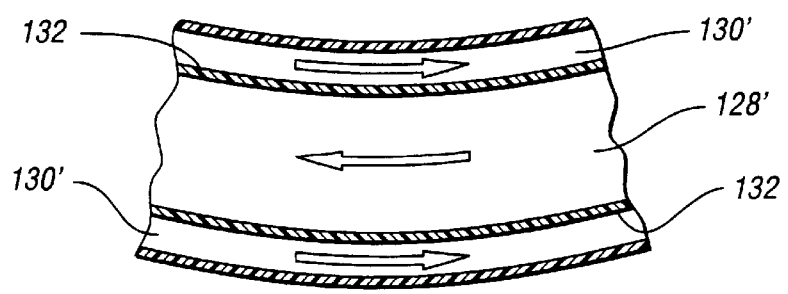
FIG. 5 is a longitudinal view of the coaxial segments of the sampling and analyzing circuits.

The direction of fluid flow through sampling circuit 104-128-108 can be in either direction, as can the direction of gas flow through analyzing circuit 130. However, in the preferred embodiment, the direction of flow through sampling circuit 104-128-108 and analyzing circuit 130 will be opposite at membrane 132, as seen in FIG. 5, in order to effect a counter-current flow. The rate of equilibration of two gas mixtures, each contained within their own space but separated by a gas-permeable membrane, is not only proportional to the rate of convective motion of the two gas mixtures past the membrane, but also depends on the direction of flow of the two gas mixtures relative to one another. Counter-current flow further expedites the equilibration process and potentially increases the responsiveness and sensitivity of the measurement of tissue pCO, and pH.

A sensor 58, with characteristics as described previously, may be provided at any point in analyzing circuit 130 as a means for continuously quantifying the level, percentage, concentration, or partial pressure of $CO_2$ gas. Auxiliary valves 136 may be used to permit either circuit to be flushed with ambient air, a gas mixture or a liquid. In analyzing circuit 130, flushing with ambient air allows sensor 58 to be calibrated to a near zero level of $CO_2$. $CO_2$ measurements may be corrected for the effects of pressure fluctuations as measured by a pressure sensing means such as a pressure transducer 138, with characteristics as described previously for pressure transducer 54, within analyzing circuit 130.

Electronic circuit 60, control and display panel 72, and their associated components, with characteristics as described previously, are utilized in the same manner in the extracorporeal CRGT system as in the intracorporeal CRGT system.

The extracorporeal CRGT system has been described in terms of its capability for $CO_2$ measurement. In general, an extracorporeal recirculating gas tonometry system as described above can also be used to determine the concentration of any gas that may be contained within the tissue of the body. This may be accomplished by ensuring that membrane 132 is permeable to the particular gas to be measured, and that sensor 58 will detect and quantify the level of the particular gas to be measured.

It is understood, of course, that while the form of the invention herein shown and described constitutes a preferred embodiment of the invention, it is not intended to illustrate all possible forms thereof. It will also be understood that the words used are words of description rather than limitation, and that various changes may be made without departing from the spirit and scope of the invention disclosed.

What is claimed is:

1. A tonometry catheter apparatus comprising:
    an elongate flexible tube having a proximal extracorporeal end and a distal intracorporeal end;
    the distal end of the tube having
        a distensible, inflatable, gas-permeable tonometry vessel, the vessel and the distal end defining therebetween a space which is filled with a gas,
        an egress orifice in communication with the space, through which gas may enter the vessel,
        an egress lumen with a distal end and a proximal end, the distal end being in communication with the egress orifice,
        an ingress orifice in communication with the space, through which the gas may exit the vessel, and
        an ingress lumen with a distal end and a proximal end, the distal end being in communication with the ingress orifice,
        wherein the diameter of the ingress orifice is larger than the diameter of the egress orifice so as to prevent overdistention of the vessel;
    the proximal end of the tube having
        a propeller for propelling gas into the vessel, the propeller being selected from a group consisting of a peristaltic pump, a roller pump, an impeller pump, a blower, a fan, a circulator, and their equivalents,
        a quantifier for continuously quantifying the level of gas exiting the vessel, and
        a hollow connecting member linking the propeller and the quantifier to define with the vessel, the ingress lumen, and the egress lumen a closed circuit through which the gas may continuously recirculate, thereby resulting in a substantially error-free, stable reading of gas composition within the circuit.

2. The tonometry catheter apparatus of claim 1, wherein the diameter of the ingress lumen is larger than the diameter of the egress lumen so as to prevent overdistension of the vessel.

3. The tonometry catheter apparatus of claim 1, further comprising a device for injecting gas into the circuit or aspirating gas from the circuit.

4. The tonometry catheter apparatus of claim 3, wherein the device is actuated automatically to maintain an optimal level of pressure within the circuit.

5. A tonometry catheter apparatus comprising:
    an elongate flexible tube having a proximal extracorporeal end and a distal intracorporeal end;
    the distal end of the tube having
        a distensible, inflatable, gas-permeable tonometry vessel, the vessel and the distal end defining therebetween a space which is filled with a gas,
        an egress orifice in communication with the space, through which gas may enter the vessel,
        an egress lumen with a distal end and a proximal end, the distal end being in communication with the egress orifice,
        an ingress orifice in communication with the space, through which the gas may exit the vessel, and
        an ingress lumen with a distal end and a proximal end, the distal end being in communication with the ingress orifice,
    the proximal end of the tube having
        a propeller for propelling gas into the vessel, the propeller being selected from a group consisting of a peristaltic pump, a roller pump, an impeller pump, a blower, a fan, a circulator, and their equivalents,
        a quantifier for continuously quantifying the level of $CO_2$ gas exiting the vessel, and
        a hollow connecting member linking the propeller and quantifier to define with the vessel, the ingress lumen, and the egress lumen a closed circuit through which the gas may continuously recirculate, thereby resulting in a substantially error-free, stable reading of gas composition within the circuit;

wherein the gas contained within the circuit comprises a mixture of a nontoxic gas and a physiologic concentration of $CO_2$ gas prior to placement of the vessel within the body of a patient so as to facilitate equilibration with the gas concentration adjacent the vessel.

6. The tonometry catheter apparatus of claim 5, wherein the nontoxic gas includes helium.

7. The tonometry catheter apparatus of claim 5, further comprising a device for injecting gas into the circuit or aspirating gas from the circuit.

8. The tonometry catheter apparatus of claim 7, wherein the device is actuated automatically to maintain an optimal level of pressure within the circuit.

9. A tonometry catheter apparatus comprising:

a sampling circuit and an analyzing circuit through which fluid may continuously recirculate;

the sampling circuit having a proximal end and a distal end, the distal end of the sampling circuit in communication with a space which is filled with a fluid to be sampled, an ingress lumen in communication with the space, through which fluid may exit the space and enter the sampling circuit, and an egress lumen in communication with the space, through which the fluid may exit the sampling circuit and enter the space;

the analyzing circuit having a sensor for quantifying the level of fluid within the space;

wherein a segment of the sampling circuit and a segment of the analyzing circuit share a common interface which permits gaseous diffusion between the sampling circuit and the analyzing circuit.

10. The tonometry catheter apparatus of claim 9, further including an ingress orifice in communication with the ingress lumen and an egress orifice in communication with the egress lumen.

11. The tonometry catheter apparatus of claim 10, wherein the egress orifice is spaced apart from and upstream of the ingress orifice, so as to minimize the shunting of gas directly between the egress orifice and the ingress orifice thereby enhancing gas mixing.

12. The tonometry catheter apparatus of claim 10, wherein the ingress orifice is spaced apart from and upstream of the egress orifice, so as to minimize the shunting of gas directly between the ingress orifice and the egress orifice thereby enhancing gas mixing.

13. The tonometry catheter apparatus of claim 10, wherein the diameter of the ingress orifice is larger than the diameter of the egress orifice, so as to prevent the overdistention of a hollow organ into which the catheter is placed.

14. The tonometry catheter apparatus of claim 9, wherein the diameter of the ingress lumen is larger than the diameter of the egress lumen, so as to prevent the overdistension of a hollow organ into which the catheter is placed.

15. The tonometry catheter apparatus of claim 9, wherein the sensor quantifies the level of $CO_2$ gas within the space.

16. The tonometry catheter apparatus of claim 9, wherein the sensor provides real time trending information of the gas level in a tissue or organ of interest.

17. The tonometry catheter apparatus of claim 9, further including a device for displaying one or more variables indicative of physiological condition of the patient.

18. The tonometry catheter apparatus of claim 9, wherein the segment of the sampling circuit and the segment of the analyzing circuit sharing the common interface are parallel.

19. The tonometry catheter apparatus of claim 9, wherein the segment of the sampling circuit and the segment of the analyzing circuit sharing the common interface are coaxial.

20. The tonometry catheter apparatus of claim 9, further comprising at least one propeller for propelling gas through the sampling and analyzing circuits.

21. The tonometry catheter apparatus of claim 20, wherein the at least one propeller is selected from a group consisting of a peristaltic pump, roller pump, diaphragm pump, impeller pump, blower, compressor, fan, circulator, and other types of pumps.

22. The tonometry catheter apparatus of claim 9, further including a pressure sensor in communication with the sampling circuit for quantifying pressure in the sampling circuit.

23. The tonometry catheter apparatus of claim 9, further including one or more pressure relief valves in communication with the sampling circuit to regulate pressure within the sampling circuit.

24. The tonometry catheter apparatus of claim 9, further including a pressure sensor in communication with the analyzing circuit for quantifying pressure in the analyzing circuit.

25. The tonometry catheter apparatus of claim 9, further comprising one or more safety pressure relief lumens, each having a distal end and a proximal end, each distal end opening into a plurality of orifices, which may be proximate to the distal tip thereof along the tonometry catheter near its distal tip, none of the orifices communicating with the ingress lumen or with the egress lumen.

26. The tonometry catheter apparatus of claim 25, further including a pressure sensor in communication with the one or more safety pressure relief lumens for quantifying pressure in the safety pressure relief lumens and detecting undesirable or hazardous increases in pressure within a body cavity of a human subject in whom the catheter has been inserted.

27. The tonometry catheter apparatus of claim 25, further including one or more pressure relief valves in communication with the one or more safety pressure relief lumens to regulate pressure within the safety pressure relief lumens in the event of malfunction that could otherwise lead to an undesirable and hazardous progressive accumulation of gas within a body cavity of a human subject in whom the catheter has been inserted.

28. The tonometry catheter apparatus of claim 9, wherein gas contained within the analyzing circuit comprises ambient air prior to placement of the catheter within the body of a patient, and after equilibration the gas comprises a mixture having a composition approximating that of body tissues adjacent the catheter.

29. The tonometry catheter apparatus of claim 9, wherein gas contained within the analyzing circuit comprises a mixture of a nontoxic gas and a physiologic concentration of $CO_2$ gas prior to placement of the catheter within the body of a patient so as to facilitate equilibration, and after equilibration the gas comprises a mixture having a composition approximating that of body tissues adjacent the catheter.

30. The tonometry catheter apparatus of claim 29, wherein the nontoxic gas includes helium.

31. The tonometry catheter apparatus of claim 9, further comprising a device for injecting gas into the analyzing circuit and aspirating gas from the analyzing circuit.

32. The tonometry catheter apparatus of claim 31, wherein the device is actuated automatically to maintain an optimal level of pressure within the analyzing circuit.

33. The tonometry catheter apparatus of claim 9, wherein fluid flow within the sampling circuit occurs in a direction opposite to fluid flow within the analyzing circuit.

34. A method for indirect monitoring of organ or tissue gas composition comprising:

providing a catheter having an elongate flexible tube, the tube having a distal end and a proximal end;

introducing the catheter into an organ of interest so that the tube distal end is disposed at a desired sampling site;

positioning the tube distal end at the sampling site for a length of time sufficient to allow fluid at the sampling site to enter an ingress orifice provided within the tube;

circulating the fluid within a sampling circuit defined by the ingress orifice, an egress orifice, and a first hollow member connecting the ingress and egress orifices;

allowing gas to diffuse out the sampling circuit into a second hollow member which is filled with a gas and defines a closed analyzing circuit via a common, gas-permeable interface disposed therebetween; and analyzing gas within the analyzing circuit to determine the gas composition of the organ into which the catheter was placed.

35. The method of claim 34, wherein introducing the catheter into an organ of interest includes inserting the catheter by a transnasal, transoral, transrectal, surgical, or other route of placement into some portion of the gastrointestinal tract, which includes the esophagus, stomach, duodenum, small intestines, jejunum, ileum, colon or large intestine, or rectum, or other organ of interest of the body.

36. The method of claim 34, wherein analyzing gas within the analyzing circuit includes continuously monitoring the level, percentage, proportion, or partial pressure of the gas.

37. The method of claim 36, wherein continuously monitoring the gas includes continuously monitoring the level, percentage, proportion, or partial pressure of $CO_2$ gas.

38. The method of claim 37, further including determining the intracellular pH of the organ or tissue at or near the sampling site on a continuous basis from the level of $CO_2$ gas and a measure or estimate of body bicarbonate concentration or total $CO_2$ content of the blood, serum, plasma, or tissue.

39. The method of claim 34, further comprising allowing entry of the bicarbonate ion concentration of the blood, serum, plasma, or tissue into the electronic portion of the system.

40. The method of claim 34, further comprising displaying and/or recording the measured and/or derived values on a continuous basis.

41. The method of claim 34, further comprising triggering an audible or visual alarm when a malfunction in the system is sensed, or when the measured or derived values are above or below pre-selected critical values.

* * * * *